United States Patent
Bernhardt et al.

(10) Patent No.: US 8,199,162 B2
(45) Date of Patent: Jun. 12, 2012

(54) CONTRAST INCREASE IN X-RAY PROJECTION IMAGES AND/OR IN TOMOGRAPHICALLY RECONSTRUCTED VOLUMES BY DECONVOLUTION OF THE PROJECTION IMAGES

(75) Inventors: Philipp Bernhardt, Forchheim (DE); Bernhard Scholz, Heroldsbach (DE)

(73) Assignee: Siemens Aktiengesellschaft, München (DE)

( * ) Notice: Subject to any disclaimer, the term of this patent is extended or adjusted under 35 U.S.C. 154(b) by 363 days.

(21) Appl. No.: 12/549,039

(22) Filed: Aug. 27, 2009

(65) Prior Publication Data

US 2010/0053203 A1    Mar. 4, 2010

Related U.S. Application Data

(60) Provisional application No. 61/092,864, filed on Aug. 29, 2008.

(30) Foreign Application Priority Data

Aug. 28, 2008  (DE) .......................... 10 2008 044 678
Sep. 17, 2008  (DE) .......................... 10 2008 047 629

(51) Int. Cl.
     *G09G 5/00*    (2006.01)
(52) U.S. Cl. ...................................... 345/581
(58) Field of Classification Search .................. 345/581; 378/62
     See application file for complete search history.

(56) References Cited

U.S. PATENT DOCUMENTS 6,166,384 A * 12/2000 Dentinger et al. ....... 250/370.09
2005/0002550 A1 * 1/2005 Jabri et al. .................... 382/131

FOREIGN PATENT DOCUMENTS

EP    1004983 A1    5/2000

OTHER PUBLICATIONS

Abbot, P., A. Shearer, T. O'Doherty, and W. Van Der Putten. "Image Deconvolution as an Aid to Mammographic Artefact Identification I: Basic Techniques." Proc. SPIE 3661 (Feb. 1999): 698-709.*
Seibert, J. A., and J. M. Boone. "X-ray Scatter Removal by Deconvolution." Medical Physics 15.4 (1988): 567-575.*

* cited by examiner

*Primary Examiner* — Xiao M. Wu
*Assistant Examiner* — Scott E Sonners

(57)    ABSTRACT

The invention relates to a method and a device for increasing contrast in medical images generated by an imaging system featuring an x-ray source and a detector. The detector detects x-rays of the x-ray source and converts image signals from the x-rays. The image signals are transferred to a control and processing unit for processing. Deconvolution of the image signals is carried out by application of an inverse modulation transfer function modified by a regularization. At least a volume image can be reconstructed from the deconvolved image signals.

11 Claims, 4 Drawing Sheets

Original projection image O1

Deconvoluted projection image E1

Original projection image O1

Deconvoluted projection image E1

Original projection image 02

Deconvoluted projection image E2 window center/ width 150/300
layer thickness 5 mm

----- Deconvoluted, undershooting    ——— Deconvoluted, undershooting, corrected

CONTRAST INCREASE IN X-RAY PROJECTION IMAGES AND/OR IN TOMOGRAPHICALLY RECONSTRUCTED VOLUMES BY DECONVOLUTION OF THE PROJECTION IMAGES

CROSS REFERENCE TO RELATED APPLICATIONS

The present application claims the benefit of a provisional patent application filed on Aug. 29, 2008, and assigned application No. 61/092,864. The present application also claims the benefit of German application No. 10 2008 044 678.5 filed Aug. 28, 2008 and German application No. 10 2008 047 629.3 filed Sep. 17, 2008. All of the applications are incorporated by reference herein in their entirety.

FIELD OF THE INVENTION

The invention relates to a method for increasing contrast in medical images or in tomographically reconstructed volumes by deconvolution of the projection images.

BACKGROUND OF THE INVENTION

The energy of an x-ray beam hitting a generally flat detector will not be converted completely into an electrical signal at the contact point (x, y: Cartesian coordinates of the contact point) and at the locations lying directly beneath it with the same lateral coordinates (x, y). The scintillation process generates electrical signals in adjacent locations and even in locations further away. I.e. an x-ray beam which hits a pixel with the coordinates (x, y), generates electrical signals in the contacted pixel, in the surrounding pixels and even in pixels further away. This non-locality of the energy conversion leads to image smear and thus to reductions in contrast.

SUMMARY OF THE INVENTION

The object of the invention lies in improving the procedure described above.

The smearing of the signal generation presented above can be described mathematically by convolving the ideal signal with a smear function. The smear function is the modulation transfer function (MTF) of the detector. The removal of smearing from the projection image ideally occurs through deconvolution with the inverse MTF. In reality the deconvolution with the inverse MTF does not produce the desired image. Instead noise structures are drastically accentuated, so that the image deconvolved in this way is unusable. As a result the MTF must be suitably modified in order to obtain de-smeared image results with a noise level which approximately or entirely corresponds to that of the original projection image. With the improved projection images a tomographic, as a rule, three-dimensional reconstruction can then be undertaken. The reconstruction results with these types of improved projection images without exception exhibit markedly improved contrast.

The inventive process is as follows:
a. The de-smearing of the project images originating from CT or C-arm or elsewhere.
b. Executing the de-smearing with the detector MTF or with suitably modified detector MTFs.
c. Image reconstruction with the de-smeared projection images.

The description below shows how suitable de-smear functions are able to be obtained. In the frequency space the de-smearing is a multiplication of the Fourier-transformed ideal image by the Fourier-transformed smear function. As a result the deconvolved image in the frequency space is produced from the division of the Fourier-transformed measured image by the Fourier-transformed smear function or by multiplication by the inverse Fourier transformed smear function. Since however the Fourier-transformed smear function for higher local frequencies tends towards zero, its inverse tends towards infinite. The inverse Fourier-transformed smear function is thus unusable since it amplifies high local frequencies in the image over all dimensions Making the frequency behavior of the inverse Fourier-transformed smear function finite is referred to below as regularizing. This regularizing modifies the Fourier-transformed MTF so that the low frequency behavior remains unchanged and so that the MTF converges for high frequencies towards any given predeterminable finite non-negative value. Such a regularized MTF is able to be inverted and tends for high frequencies towards a finite value which is determined by the regularization specification.

The regularization can naturally be conducted in a different way. A specific choice is made by the regularization specification. A possible regularization specification is as follows:

$$f(v) \to f_{reg}(v) = (f(v) + R(v))/N.$$

The meanings here are as follows
v the two-dimensional local frequency vector
f the MTF of the detector
R regularization function
$f_{reg}$ the regularized MTF
N a normalizing factor so that the following applies for the zero frequencies:

$$f(0) = f_{reg}(0).$$

The previous observations are two-dimensional observations since projection images and MTF are two-dimensional functions. For this reason the above frequency dependencies are written vectorially (the frequency is a vector in the 2D frequency space).

Since the two-dimensional deconvolution can be processing time-intensive, it is useful to only undertake the deconvolution row-by-row or column-by-column. Such cases then involve one-dimensional deconvolutions. The row and column MTFs of the detector are also regularized as above.

As a result of the deconvolution undershoots can occur in the deconvolved images. Undershoots are function areas of the image data with negative values. Since these values are unphysical, they must be corrected, i.e. these values must be replaced by non-negative values. The replacement is undertaken such that essentially the structure is to be obtained, see FIG. 4.

The invention is characterized by the following advantages:

The result of the measures described above is contrast improvement in the x-ray projection images and in volumes reconstructed with computer tomography processes, see FIGS. 1 and 2. It is especially shown that in reconstructed cephalograms the bone soft part contrast increases markedly and the so-called bone detritus effect is rectified.

BRIEF DESCRIPTION OF THE DRAWINGS

One or more exemplary embodiments of the invention will be described below with reference to a drawing.
In the drawing the figures are as follows.

DETAILED DESCRIPTION OF THE INVENTION

Figure 5:
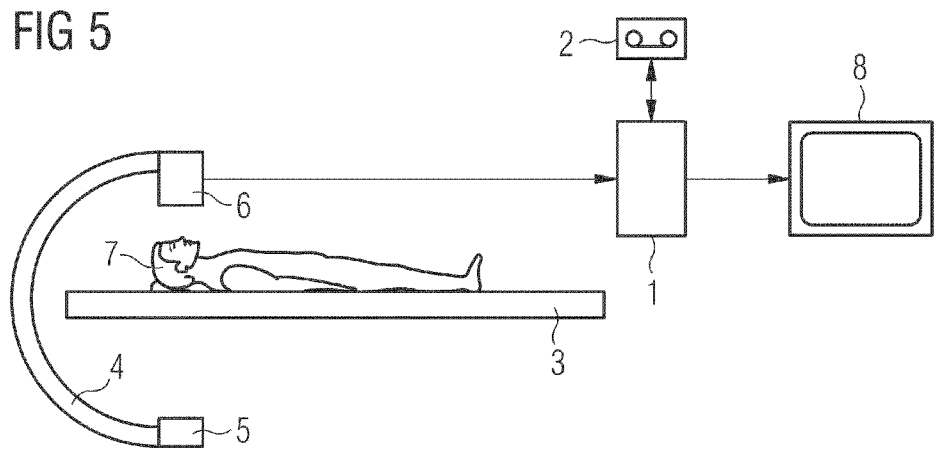
FIG. 5 an imaging system, preferably and x-ray diagnostic device embodied for executing the inventive method.

FIG. 5 shows an example of an imaging system, especially an x-ray diagnostic device which features a C-arm 4 supported so that it can rotate on a stand not shown in the figure, on the ends of which are an x-ray source 6, for example and x-ray transmitter, and a preferably extensively embodied x-ray image detector 5. Within the context of the invention the imaging system can also involve an x-ray C-arm system for example, an x-ray biplanar device or a computer tomograph.

In the beam entry of the x-ray source 6 is located a patient support table 3 for receiving an area of a patient 7 to be examined. Connected to the x-ray diagnostic device is an imaging system with a control and processing unit 1 with a memory unit 2 or is connected remotely if necessary, which receives and processes the image signals of the x-ray image detector 5. The processed image signals can then be displayed on a display device 8 connected to the imaging system 1.

The imaging system 2 can feature one or more hardware or software modules not shown in the figure for contrast increase in medical images according to the invention. Furthermore the imaging system can be operated by a computer program product comprising at least one software module or software for executing the method described above. This computer program product can preferably be stored for installation purposes on a memory medium, especially a DVD data medium, with the data on the memory medium able to be transmitted or copied into the memory unit 2 of the imaging system.

The invention is not restricted to the exemplary embodiment given above. It is equally conceivable for the imaging system 2 to be connected to a workstation e.g. via a computer network. In this case the invention can then be used on the workstation.

Figure 1:
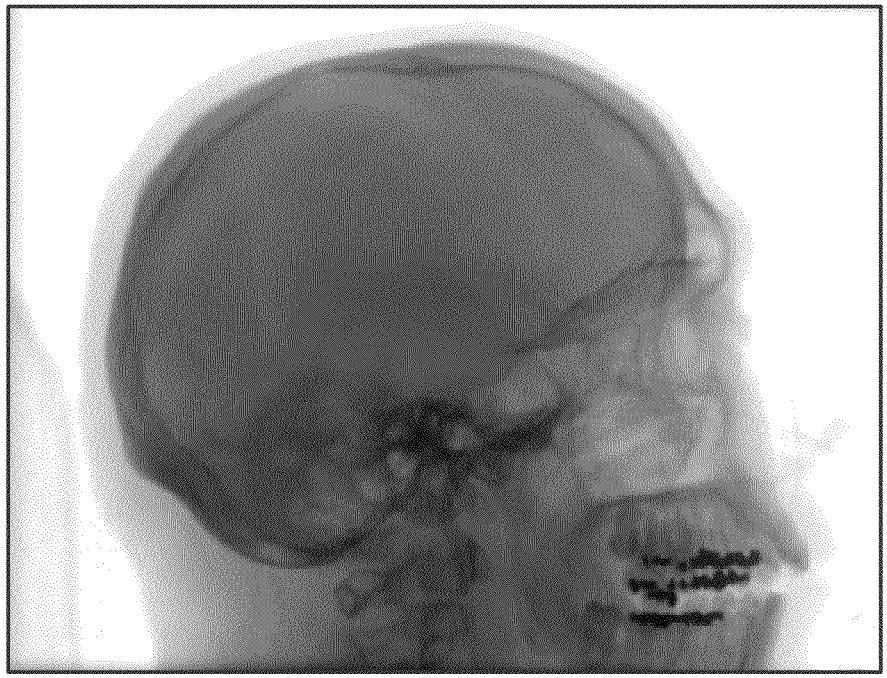
FIG. 1 a comparison of original projection image and deconvolved projection image, FIG. 2 a reconstruction without and with row and column-deconvolved projection images, FIG. 3 an example of the deconvolution of a projection data row and FIG. 4 an example for a row deconvolution of a projection image with undershoot correction.
Figure 1:
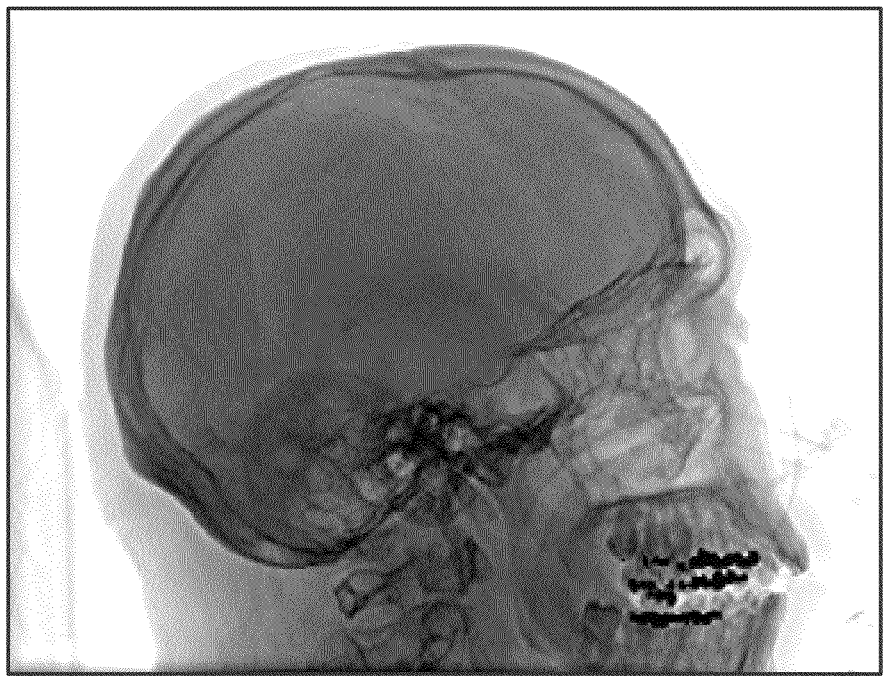
Figure 2:
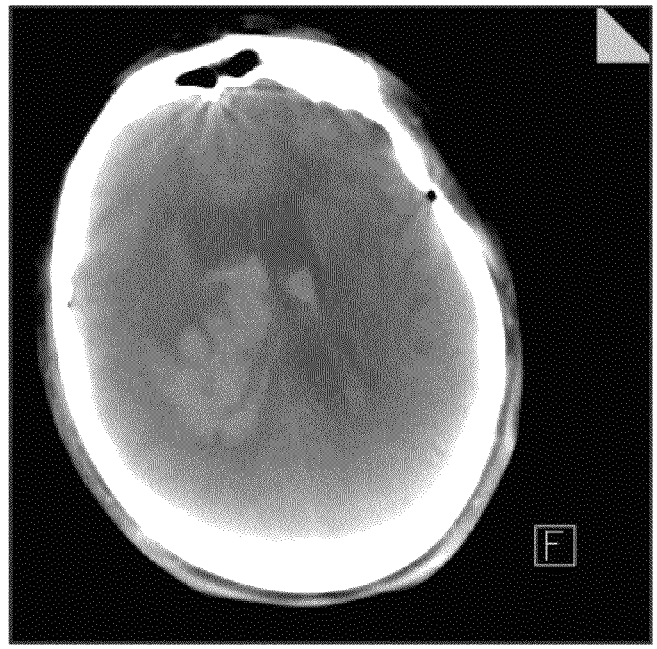
Figure 2:
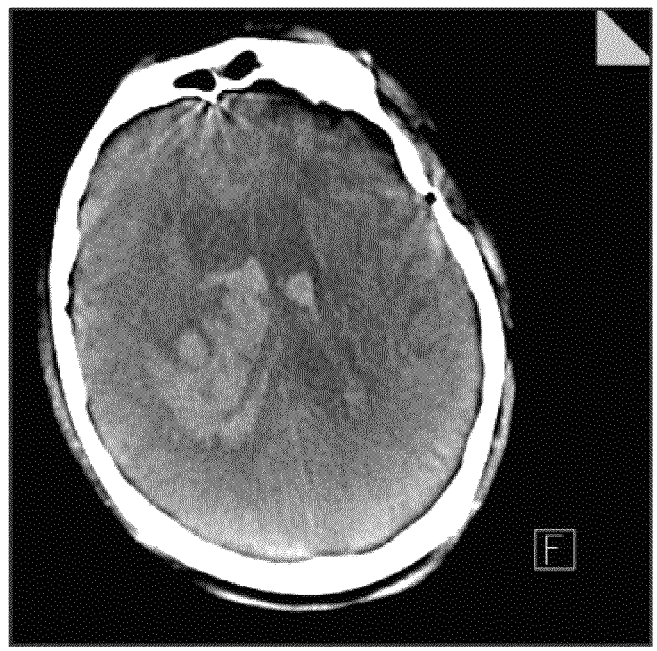

FIG. 1 shows a comparison of an original projection image O1 and an inventively deconvolved projection image E1. In FIG. 2 a reconstruction without and with row and column-deconvolved projection images (original projection O2 and deconvolved projection image E2) is shown.

The smearing of the signal generation shown at the start can be described mathematically by convolving the "ideal" signal with a smear function. The smear function is the modulation transfer function (MTF) of the detector. The de-smearing of the projection image is undertaken by deconvolution with the inverse MTF. In reality the deconvolution with the inverse MTF does not produce the desired image. Instead noise structures are drastically accentuated, so that the image deconvolved in this way is unusable. As a result the MTF must be suitably modified in order to obtain de-smeared image results with a noise level which approximately or entirely corresponds to that of the original projection image e.g. O1 or O2. With the improved projection images a tomographic, as a rule, three-dimensional reconstruction can then be undertaken. The reconstruction results with these types of improved projection images without exception exhibit markedly improved contrast.

The inventive process is as follows:
1. The de-smearing of the project images originating from CT or C-arm or elsewhere.
2. Executing the de-smearing or deconvolution with the detector MTF or with suitably modified detector MTFs.
3. Optionally an image reconstruction with the de-smeared projection images.

The description below shows how suitable de-smear functions are able to be obtained. In the frequency space the de-smearing is a multiplication of the Fourier-transformed ideal image by the Fourier-transformed smear function or MTF. As a result the deconvolved image in the frequency space is produced from the division of the Fourier-transformed measured image by the Fourier-transformed smear function or by multiplication by the inverse Fourier transformed smearing function. Since however the Fourier-transformed smearing function for higher local frequencies tends towards zero, its inverse tends towards infinite. The inverse Fourier-transformed smearing function is thus unusable since it amplifies high local frequencies in the image over all dimensions.

Making the frequency behavior of the inverse Fourier-transformed smearing function finite is referred to below as regularizing. This regularizing modifies the Fourier-transformed MTF so that the low-frequency behavior remains unchanged and so that the MTF, for high frequencies, converges towards an given predeterminable non-negative value. Such a regularized MTF is able to be inverted and tends for high frequencies towards a finite value which is determined by the regularization specification.

The regularization can naturally be conducted in a different way. A specific choice is made by the regularization specification. A possible regularization specification is as follows:

$$f(v) \rightarrow f_{reg}(v) = f(v) + R(v))/N.$$

The meanings here are as follows
v the two-dimensional local frequency vector
f the MTF of the detector
R regularization function
$f_{reg}$ the regularized MTF
N a normalizing factor so that the following applies for the zero frequencies:

$$f(0) = f_{reg}(0).$$

The previous observations are two-dimensional observations since projection images and MTF are two-dimensional functions. For this reason the above frequency dependencies are written vectorially (the frequency is a vector in the 2D frequency space).

Since the two-dimensional deconvolution can be processing time-intensive, it is useful to only undertake the deconvolution row-by-row or column-by-column. In this case one-dimensional deconvolutions are then involved. The row and column MTFs of the detector are likewise regularized as above. Shown in FIG. 2 is and example for a reconstruction without and with row and/or column-deconvolved projection images.

Figure 3:
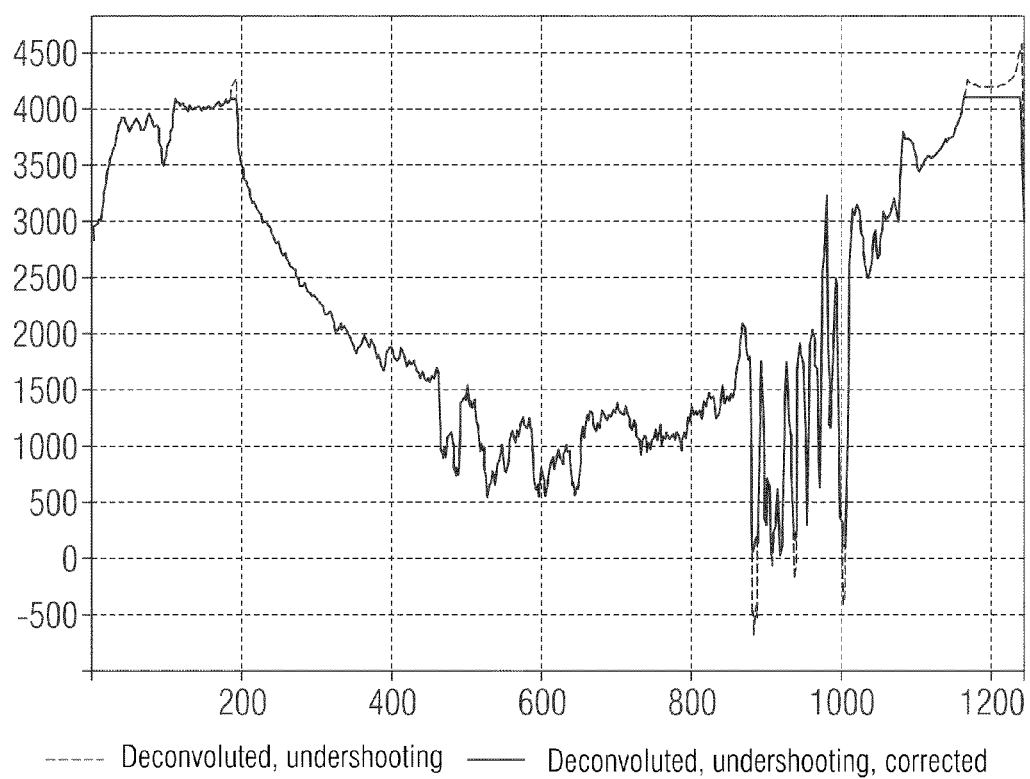
Figure 4:
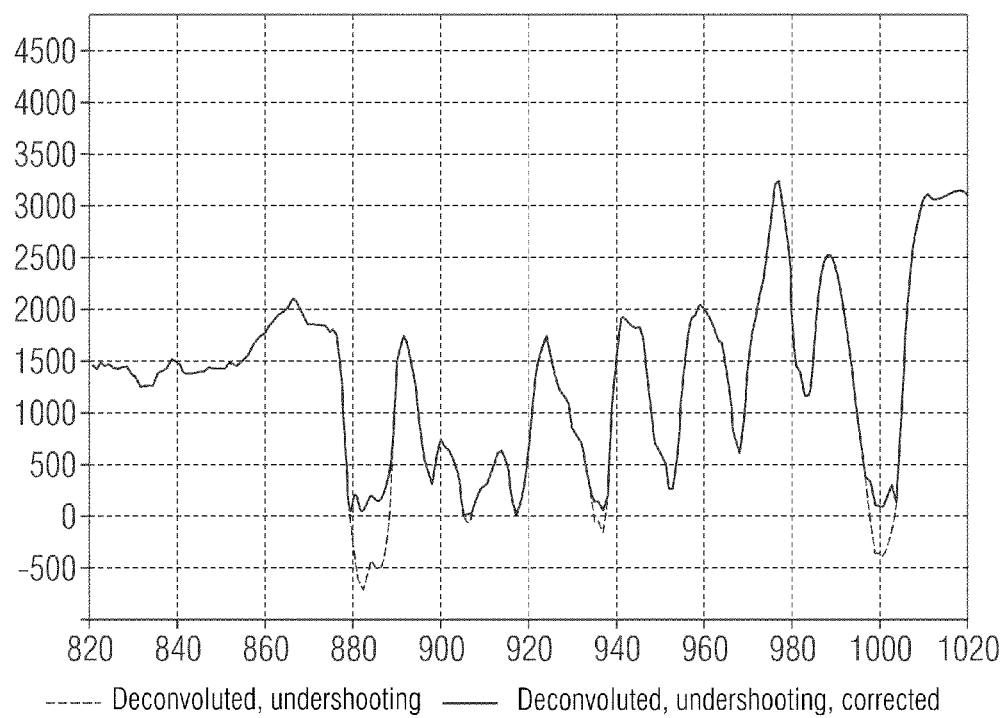

As a result of the deconvolution undershoots can occur in the deconvolved images. Undershoots are function areas of the image data with negative values. FIG. 3 shows a typical graph for the deconvolution of a projection data row which features undershoots or negative values. Since these values are unphysical, they will be corrected, i.e. these values will be replaced by non-negative values. The replacement of the negative values is undertaken such that the structure is obtained. FIG. 4 shows a typical graph for a row deconvolution of a projection image. In this case the undershoot correction in respect of the curve of the projection data has been undertaken so as to preserve the structure.

The invention claimed is:

1. A method for increasing contrast in a medical image, comprising:
    acquiring the medical image by an imaging system;
    modifying an inverse modulation transfer function by a regularization using a control and processing unit;
    applying the modified inverse modulation transfer function to image signals of the medical image using the control and processing unit; and
    deconvolving the image signals by the application,
    wherein a negative value in the deconvolved image signals is corrected by a positive value.

2. The method as claimed in claim 1, wherein a volume image is reconstructed from the deconvolved image signals.

3. The method as claimed in claim 1, wherein the medical image comprises two dimensions.

4. The method as claimed in claim 1, wherein the medical image comprises a three dimensional reconstruction.

5. The method as claimed in claim 1, wherein the medical image is acquired by row-by-row or column-by-column sampling and the deconvolving is carried out on the sampled image signals.

6. The method as claimed in claim 5, wherein a two-dimensional image is reconstructed from the deconvolved image signals.

7. The method as claimed in claim 1, wherein the regularization is represented by the following specification:

$$f(v) \rightarrow f_{reg}(v) = (f(v) + R(v))/N,$$

with the following meanings
v a local frequency vector,
f a modulation transfer function of the detector,
R a regularization function,
$f_{reg}$ a regularized modulation transfer function, and
N a normalization factor, so that for zero frequencies the following applies:

$$f(0) = f_{reg}(0).$$

8. The method as claimed in claim 7, wherein the local frequency vector comprises one or more dimensions depending on dimensions of the medical image.

9. An imaging system, comprising:
    an x-ray source that emits x-rays;
    a detector that detects the x-rays and converts image signals from the x-rays; and
    a control and processing unit that:
        modifies an inverse modulation transfer function by a regularization,
        applies the modified inverse modulation transfer function to the image signals, and
        deconvolves the image signals by the application,
    wherein a negative value in the deconvolved image signals is corrected by a positive value.

10. The imaging system as claimed in claim 9, wherein the detector is a flat detector.

11. A computer program product stored on a memory of a control and processing unit for executing a method of increasing contrast in a medical image, the method comprising:
    acquiring the medical image by an imaging system;
    modifying an inverse modulation transfer function by a regularization using the control and processing unit;
    applying the modified inverse modulation transfer function to image signals of the medical image using the control and processing unit; and
    deconvolving the image signals by the application using the control and processing unit,
    wherein a negative value in the deconvolved image signals is corrected by a positive value.

* * * * *